United States Patent [19]

Sakai et al.

[11] 4,332,948
[45] Jun. 1, 1982

[54] NOVEL HYDRAZONE COMPOUNDS AND PROCESS FOR PREPARING THE SAME

[75] Inventors: Kiyoshi Sakai; Mitsuru Hashimoto; Kyoji Tsutsui, all of Numazu, Japan

[73] Assignee: Ricoh Company, Ltd., Tokyo, Japan

[21] Appl. No.: 149,752

[22] Filed: May 14, 1980

[30] Foreign Application Priority Data

May 25, 1979 [JP] Japan .................................. 54-64033

[51] Int. Cl.³ .................. C07D 333/36; C07C 109/12
[52] U.S. Cl. .................................... 542/417; 542/415; 564/251
[58] Field of Search .................... 260/566 B; 542/417, 542/415; 564/251

[56] References Cited

U.S. PATENT DOCUMENTS

| | | | |
|---|---|---|---|
| 2,786,044 | 3/1957 | Warner et al. | 260/566 B |
| 3,158,608 | 11/1964 | Raoe | 542/417 |
| 3,923,506 | 12/1975 | Bergfjord et al. | 260/566 B |
| 3,978,049 | 8/1976 | Schirmann et al. | 260/566 B |
| 4,150,987 | 4/1979 | Anderson | 260/566 B |

FOREIGN PATENT DOCUMENTS

| | | |
|---|---|---|
| 2919791 | 11/1979 | Fed. Rep. of Germany . |
| 930988 | 7/1963 | United Kingdom . |
| 1156151 | 6/1969 | United Kingdom . |
| 1324684 | 7/1973 | United Kingdom . |

OTHER PUBLICATIONS

Mazza et al., Il Faimaco, Ed. Sc. 31 (5), p. 334-344.
Chem. Abstracts, 9th Collective Index, p. 1994 CS.

Primary Examiner—Arthur P. Demers
Attorney, Agent, or Firm—Oblon, Fisher, Spivak, McClelland & Maier

[57] ABSTRACT

Hydrazone compounds having the general formula

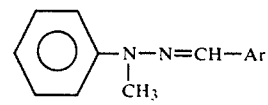

wherein Ar is selected from the group consisting of a naphthalene ring radical, substituted naphthalene ring radicals, an anthracene ring radical, substituted anthracene ring radicals, styryl, substituted styryls, a pyridine radical, a furan ring radical and a thiophene ring radical.

The hydrazone compounds can be prepared by allowing 1-methyl-1-phenylhydrazine having the formula

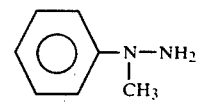

to react with an aldehyde represented by the general formula Ar-CHO, wherein Ar is the same as mentioned above at a substantially equal molar ratio in an organic solvent selected from the group consisting of lower alcohols, cyclic ethers, cellosolves, N,N-dimethylforamide and acetic acid, in the presence of an acid catalyst, by heating and refluxing the reaction mixture.

The hydrazone compounds are extremely useful as charge transport materials for use in electrophotographic photoconductors of the type comprising an electroconductive support material and a photosensitive layer containing a charge generation material and a charge transport material.

4 Claims, 9 Drawing Figures

NOVEL HYDRAZONE COMPOUNDS AND PROCESS FOR PREPARING THE SAME

BACKGROUND OF THE INVENTION

The present invention relates to novel hydrazone compounds and to their preparation and use, and more particularly to hydrazone compounds represented by the general formula

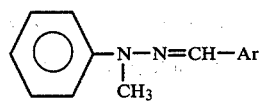

wherein Ar represents a condensed ring, such as a naphthalene ring, an anthracene ring, or their substituted rings; a styryl group or its substituted groups; or a heterocyclic ring, such as a pyridine ring, a furan ring or a thiophene ring; and to a process for preparing the hydrazone compounds by allowing aldehydes represented by the formula Ar-CHO, wherein Ar represents the same as mentioned above, to react with 1-methyl phenylhydrazine represented by the formula

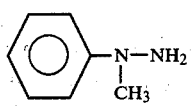

in accordance with the following equation:

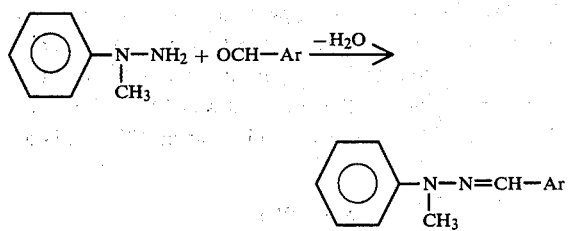

The thus prepared hydrazone compounds are extremely useful charge transport materials for use in, for example, electrophotographic photoconductors of the type comprising an electroconductive support material and a photosensitive layer containing a charge generation material and a charge transport material.

As is well known, a variety of substances with —NH$_2$ groups condense with carbonyl compounds to give >C=N— compounds and water. These reactions usually require catalysts. The condensation reactions may proceed through initial addition of an amine reagent to the carbonyl group with subsequent elimination of water from the two molecules, whereby an unsaturated nitrogen-containing derivative is formed:

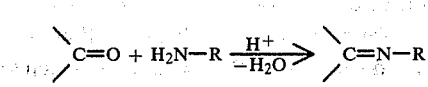

By the above-mentioned condensation reactions, many hydrazone compounds have been prepared and some of them have been found to be useful as electrophotographic materials as is disclosed in British Pat. No. 930,988, No. 933,363, No. 1,156,151 and No. 1,324,684 and U.S. Pat. No. 3,756,884.

However, no prior art reference of which we are aware suggests the hydrazone compounds according to the present invention and their preparation and use.

SUMMARY OF THE INVENTION

It is therefore an object of the present invention is to provide hydrazone compounds represented by the following formula

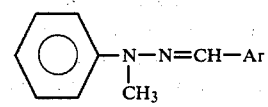

wherein Ar represents a condensed ring, such as a naphthalene ring, an anthracene ring or their substituted rings; a styryl group or its substituted groups; or a heterocyclic ring, such as a pyridine ring, a furan ring or a thiophene ring.

Another object of the present invention is to provide a process for preparing the above-mentioned hydrazone compounds by allowing aldehydes represented by the general formula AR-CHO, wherein Ar represents the same as mentioned above, to react with 1-methyl phenylhydrazine represented by the formula

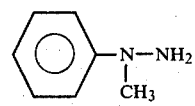

According to the present invention, the hydrazone compounds are prepared by allowing the aldehydes to react with the 1-methyl phenylhydrazine in an appropriate solvent in the presence of an acid catalyst. The thus prepared hydrazone compounds are purified by recrystallization from a suitable solvent. The thus obtained pure hydrazone compounds are used as charge transport materials in combination with a variety of charge generation materials to form electrophotographic photoconductive materials, whereby electrophotographic photoconductors having high photosensitivities can be obtained.

DETAILED DESCRIPTION OF THE PREFERRED EMBODIMENTS

Figure 1:
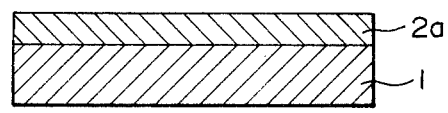
FIG. 1 through FIG. 3 are schematic sectional views of the electrophotographic photoconductors in which the novel hydrazone compounds according to the present invention are employed, enlarged in the direction of the thickness of each electrophotographic photoconductor.

The hydrazone compounds according to the present invention are colorless or yellow crystals at room temperature, which can be obtained easily by allowing the aldehydes represented by the general formula Ar—CHO, wherein Ar represents a condensed ring, such as a naphthalene ring, an anthracene ring or their substituted rings; an α-cinnamyl group or its substituted groups; or a heterocyclic ring, such as a pyridine ring, a furan ring or a thiophene ring, to react with 1-methyl phenylhydrazines represented by the formula $C_6H_5N(CH_3)NH_2$ substantially at a 1:1 molar ratio in an appropriate organic solvent. In these reactions, the amino groups of the hydrazines condense with the carbonyl groups of the aldehydes to give the hydrazones and water. As is well known, these condensation reactions are promoted by acid catalysts including inorganic acids, such as hydrochloric acid or dilute sulfuric acid; or organic acids, such as acetic acid, can be used. Furthermore, in the reactions, most organic solvents can be used as the reaction solvents if the above-mentioned components for the reactions are soluble in the solvents. For example, lower alcohols, such as methanol and ethanol; cyclic ethers, such as 1,4-dioxane; and tetrahydrofurane; cellosolves, such as methyl cellosolve and ethyl cellosolve; N,N-dimethylformamide; or acetic acid can be used. The reaction temperature may vary, depending upon the adopted solvent. When, N,N-dimethylformamide is used, since the above-mentioned reaction components are very soluble in that solvent, the reaction proceeds sufficiently at room temperature. On the other hand, in the case of ethanol, since the above-mentioned reaction components are less soluble in ethanol, it is preferable to heat the reaction mixture under reflux. In any case, the reaction terminates in one hour to five hours.

When the thus prepared condensation product separates out from the reaction solution, the product is filtered. When the product does not separate out, the product is caused to precipitate by addition of an diluent, such as a mixture of methanol and water, to the reaction solution. The thus obtained product is recrystallized from an appropriate solvent, so that a pure hydrazone compound is obtained.

The novel hydrazone compounds obtained according to the present invention are extremely useful as charge transport materials for use in combination with a variety of charge generation materials to form excellent electrophotographic photoconductive materials as will be explained later.

Examples of the hydrazone compounds according to the present invention are listed in the attached table 1, which includes the results of their elemental analysis and the respective melting points. Those hydrazone compounds were prepared as follows.

EXAMPLE 1

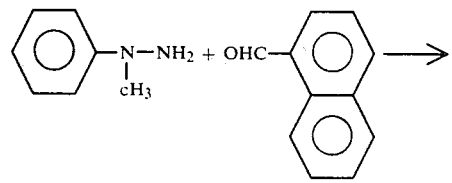

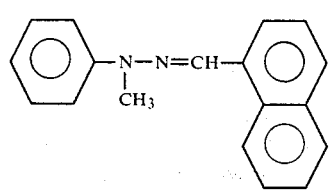

3.1 g of 1-naphthaldehyde and 2.4 g of 1-methyl-1-phenylhydrazine were added to 50 ml of ethanol. To the mixture, two or three drops of 1 N hydrochloric acid were added. The mixture was heated and refluxed for about one hour. The reaction mixture was cooled and the crystals then separated, which were then collected on a suction funnel. The thus obtained crude 1-naphthaldehyde 1-methyl-1-phenylhydrazone was recrystallized from ethanol. The yield was 3.1 g (59.6%) of light yellow needle-like crystals which melt at 92.5°–94.9° C.

EXAMPLE 2

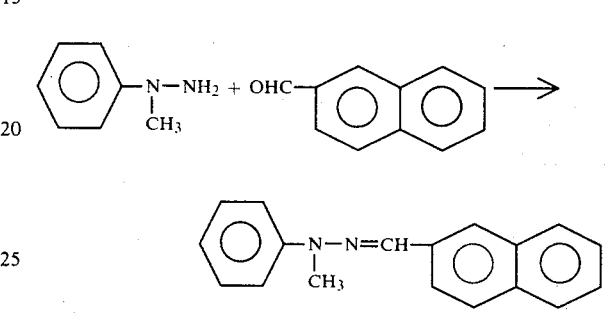

3.1 g of 2-naphthaldehyde and 2.4 g of 1-methyl-1-phenylhydrazine were added to 50 ml of ethanol. To the mixture, two or three drops of 1 N hydrochloric acid were added. The mixture was heated and refluxed for about one hour. The reaction mixture was cooled and the crystals then separated, which were then collected on a suction funnel. The thus obtained crude 2-naphthaldehyde 1-methyl-1-phenylhydrazone was recrystallized from ethyl acetate. The yield was 3.5 g (67.3%) of white needle-like crystals which melt at 172.5°–174.5° C.

EXAMPLE 3

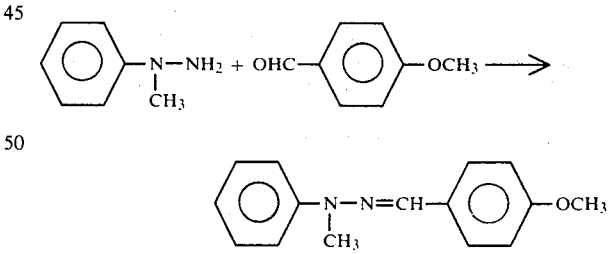

3.7 g of 4-methoxy-1-naphthaldehyde and 2.4 g of 1-methyl-1-phenylhydrazine were added to 50 ml of ethanol. To the mixture, two or three drops of 1 N hydrochloric acid were added. The mixture was heated and refluxed for about an hour. The reaction mixture was cooled and the crystals then separated, which were then collected on a suction funnel. The thus obtained crude 4-methoxy-1-naphthaldehyde 1-methyl-1-phenylhydrazone was recrystallized from ethanol. The yield was 4.0 g (69.0%) of light yellow needle-like crystals which melt at 119.5°–120.5° C.

EXAMPLE 4

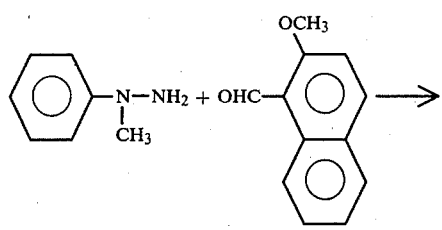

3.7 g of 2-methoxy-1-naphthaldehyde and 4.9 g of 1-methyl-1-phenylhydrazine were added to 50 ml of ethanol. To the mixture, two or three drops of 1 N hydrochloric acid were added. The mixture was heated and refluxed for about one hour. The reaction mixture was cooled and the crystals then separated, which were then collected on a suction funnel. The thus obtained crude 2-methoxy-1-naphthaldehyde 1-methyl-1-phenylhydrazone was recrystallized from ethanol. The yield was 3.7 g (63.8%) of light yellow scalelike crystals which melt at 90.5°–91.5° C.

EXAMPLE 5

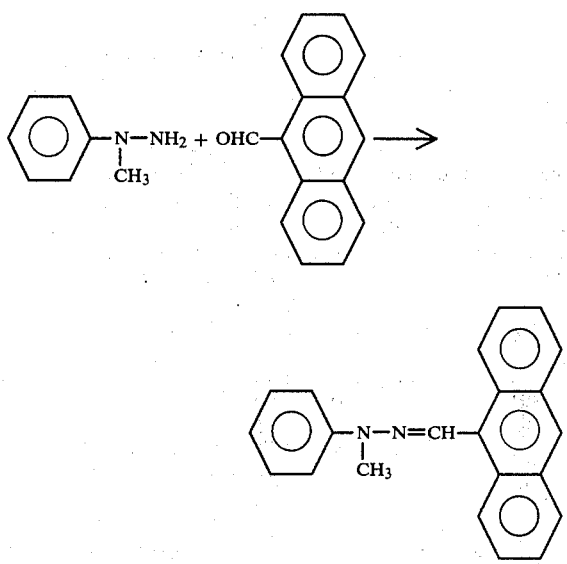

3.1 g of anthracene-9-aldehyde and 1.8 g of 1-methyl-1-phenylhydrazine were added to 50 ml of ethanol. To the mixture, two or three drops of 1 N hydrochloric acid were added. The mixture was heated and refluxed for about one hour. The reaction mixture was cooled and the crystals then separated, which were then collected on a suction funnel. The thus obtained crude anthracene-9-aldehyde 1-methyl-1-phenylhydrazone was recrystallized from ethyl acetate. The yield was 2.3 g (48.9%) of yellow needle-like crystals which melt at 162.0°–162.5° C.

EXAMPLE 6

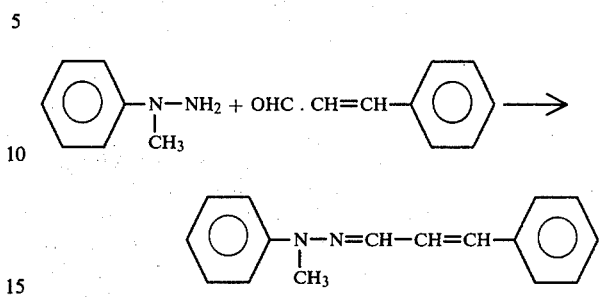

6.6 g of cinnamaldehyde and 6.1 g of 1-methyl-1-phenylhydrazine were added to 50 ml of ethanol. To the mixture, two or three drops of 1 N hydrochloric acid were added. The mixture was heated and refluxed for about one hour. The reaction mixture was cooled and the crystals then separated, which were then collected on a suction funnel. The thus obtained crude cinnamaldehyde 1-methyl-1-phenylhydrazone was recrystallized from ethanol. The yield was 6.8 g (57.6%) of light yellow needle-like crystals which melt at 113.5°–114.5° C.

EXAMPLE 7

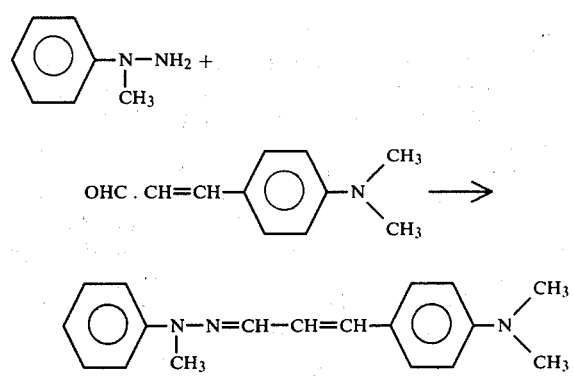

8.7 g of 4-N,N-dimethylaminocinnamaldehyde and 6.1 of 1-methyl-1-phenylhydrazine were added to 200 ml of ethanol. To the mixture, two or three drops of 1 N hydrochloric acid were added. The mixture was heated and refluxed for about one hour. The reaction mixture was cooled and the crystals then separated, which were then collected on a suction funnel. The thus obtained crude 4-N,N-dimethylaminocinnamaldehyde was recrystallized from ethyl acetate. The yield was 7.0 g (50.0%) of yellow needle-like crystals which melt at 174.0°–177.0° C.

EXAMPLE 8

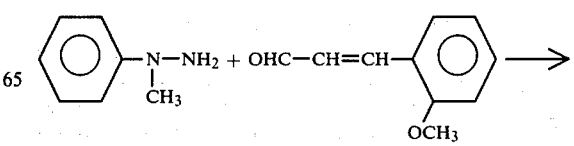

-continued

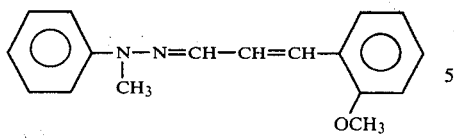

3.2 g of 2-methoxycinnamaldehyde and 2.4 g of 1-methyl-1-phenylhydrazine were added to 50 ml of ethanol. To the mixture, two or three drops of 1 N hydrochloric acid were added. The mixture was heated and refluxed for about one hour. The reaction mixture was cooled and the crystals then separated, which were then collected on a suctional funnel. The thus obtained crude 2-methoxycinnamaldehyde 1-methyl-1-phenylhydrazone was recrystallized from ethanol. The yield was 2.6 g (49.1%) of light yellow scalelike crystals which melt at 100.5°–101.5° C.

EXAMPLE 9

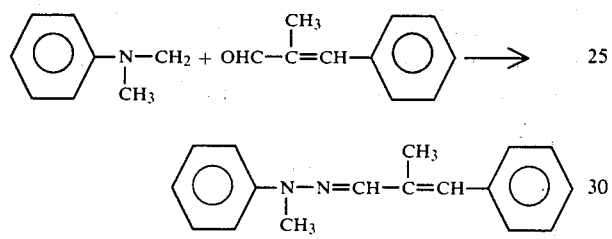

2.9 g of α-methylcinnamaldehyde and 2.4 g of 1-methyl-1-phenylhydrazine were added to 50 ml of ethanol. To the mixture, two or three drops of 1 N hydrochloric acid were added. The mixture was heated and refluxed for about one hour. The reaction mixture was cooled and the crystals then separated, which were then collected on a suction funnel. The thus obtained crude α-methylcinnamaldehyde 1-methyl-1-phenylhydrazone was recrystallized from ethanol. The yield was 3.6 g (72.0%) of light yellow scalelike crystals which melt at 111.0°–112.0° C.

EXAMPLE 10

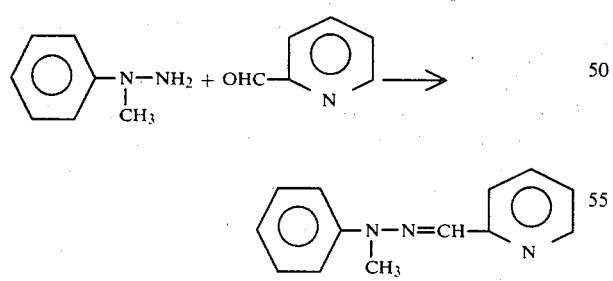

2.1 g of 2-pyridylaldehyde and 2.4 g of 1-methyl-1-phenylhydrazine were added to 50 ml of ethanol. To the mixture, two or three drops of 1 N hydrochloric acid were added. The mixture was heated and refluxed for about one hour. The reaction mixture was cooled and the crystals then separated, which were then collected on a suction funnel. The thus obtained crude 2-pyridylaldehyde 1-methyl-1-phenylhydrazone was recrystallized from cyclohexane. The yield was 2.0 g (47.3%) white needle-like crystals which melt at 53.0°–55.0° C.

EXAMPLE 11

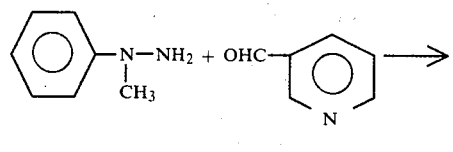

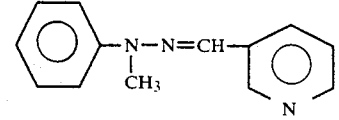

2.1 g of 3-pyridylaldehyde and 2.4 g of 1-methyl-1-phenylhydrazine were added to 50 ml of ethanol. To the mixture, two or three drops of N hydrochloric acid were added. The mixture was heated and refluxed for about one hour. The reaction mixture was cooled and the crystals then separated, which were then collected on a suction funnel. The thus obtained crude 3-pyridylaldehyde 1-methyl-1-phenylhydrazone was recrystallized from ethanol. The yield was 2.7 g (63.8%) of white needle-like crystals which melt at 96.5°–97.5° C.

EXAMPLE 12

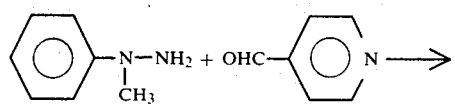

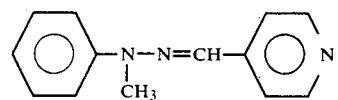

2.1 g of 4-pyridylaldehyde and 2.4 g of 1-methyl-1-phenylhydrazine were added to 50 ml of ethanol. To the mixture, two or three drops of 1 N hydrochloric acid were added. The mixture was heated and refluxed for about one hour. The reaction mixture was cooled and the crystals then separated, which were then collected on a suction funnel. The thus obtained crude 4-pyridylaldehyde 1-methyl-1-phenylhydrazone was recrystallized from ethanol. The yield was 2.5 g (59.1%) of white needle-like crystals which melt at 81.5°–82.0° C.

EXAMPLE 13

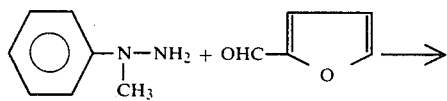

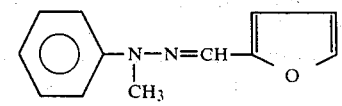

2.1 g of 2-furylaldehyde and 2.4 g of 1-methyl-1-phenylhydrazine were added to 50 ml of ethanol. To the mixture, two or three drops of 1 N hydrochloric acid were added. The mixture was heated and refluxed for about one hour. The reaction mixture was cooled and the crystals then separated, which were then collected on a suction funnel. The thus obtained crude 2-furylaldehyde 1-methyl-1-phenylhydrazone was recrystallized from petroleum ether. The hield was 1.8 g (44.9%) of white needle-like crystals which melt at 47.5°–50.0° C.

EXAMPLE 14

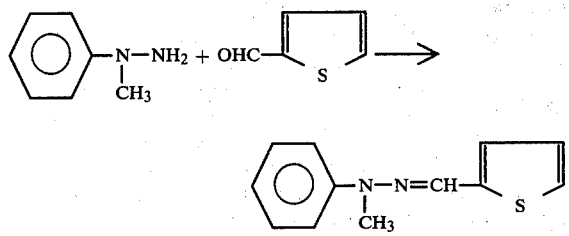

2.2 g of 2-thienylaldehyde and 2.4 g of 1-methyl-1-phenylhydrazine were added to 50 ml of ethanol. To the mixture, two or three drops of 1 N hydrochloric acid were added. The mixture was heated and refluxed for about one hour. The reaction mixture was cooled and the crystals then separated, which were then collected on a suction funnel. The thus obtained crude 2-thienylaldehyde 1-methyl-1-phenylhydrazone was recrystallized from ethanol. The yield was 2.9 g (67.0%) of light yellow needle-like crystals which melt at 81.0°–82.0° C.

Of the above-mentioned 14 hydrazone compounds, the infrared spectra of 6 hydrazone compounds are shown in FIG. 4 through FIG. 9. FIG. 4, FIG. 5, FIG. 6, FIG. 7, FIG. 8 and FIG. 9 respectively show the infrared spectrum of the hydrazone compound in Examples 1, 3, 5, 6, 12 and 14.

The inventors of the present invention have discovered that the hydrazone compounds according to the present invention are useful as electrophotographic materials.

Before explaining the specific use of the hydrazone compounds according to the present invention as electrophotographic materials, the photoconductors and materials for use in electrophotography will now be explained.

As the photoconductors for use in electrophotography, inorganic photoconductors comprising an electroconductive support material and an inorganic photoconductive material, such as selenium, cadium sulfide or zinc oxide, which is coated on the electroconductive support material, are known. Generally, in the art of electrophotography, a photoconductor is electrically charged, for example, by corona charging in the dark, and is then exposed to a light image, which selectively dissipates the charge in the illuminated areas of the photoconductor while leaving behind a latent electrostatic image in the non-illuminated areas. This latent electrostatic image may then be developed to form a visible image by depositing finely divided electroscopic marking particles called toner, which comprises coloring materials, such as dyestuff or pigments, and a binder material comprising polymeric compounds, on the photoconductor. The following fundamental characteristics are required for photoconductors for use in electrophotography:

(1) The photoconductors must be electrically chargeable to a predetermined potential in the dark.
(2) The photoconductors must retain the charge sufficiently in the dark. In other words, the dark decay of the photoconductors must be small.
(3) The charge on the photoconductors must be dissipated quickly under illumination. In other words, the light decay of the photoconductors must be great and accordingly the photosensitivity must be high.

Additionally, it is required that the photoconductors have a high mechanical strength and be workable into the desired shape.

The conventional inorganic photoconductors have some advantages, but, at the same time, they have several drawbacks. For example, the selenium photoconductor which is now widely used can satisfy the above-mentioned requirements (1), (2) and (3) to some extent. However, difficulties are encountered when producing the photoconductor and its production cost is high. More specifically, since its flexibility is poor, it is difficult to form it into various shapes. Furthermore. it is highly susceptible to heat and mechanical shocks, so care must be taken when handling it. Cadmium sulfide and zinc oxide are generally used by dispersing each of them in a binder resin. However, since they are poor in mechanical characteristics, such as smoothness, hardness, tensile strength and durability, they cannot be used repeatedly as they are. For instance, a protective layer is required, which makes the process of producing the electrophotographic element using those materials complex.

Recently, in order to eliminate the above-mentioned drawbacks of the inorganic photoconductors, a variety of electrophotographic organic photoconductors have been studied and developed and used in practice, for example, a photoconductor comprising a support material and a photosensitive layer containing poly-N-vinylcarbazole and 2,4,7-trinitrofluorene-9-on (U.S. Pat. No. 3,484,237), which is formed on the support material, a photoconductor comprising a photosensitive layer containing poly-N-vinylcarbazole sensitized by pyrylium salt dyestuff (Japanese Patent No. 48-25658), a photoconductor having a photosensitive layer consisting essentially of an organic pigment (Japanese Laid-Open Patent Application No. 47-37543), or a photoconductor having a photosensitive layer which contains as a main component an eutectic crystals complex consisting of a dyestuff and a resin (Japanese Laid-open Patent Application No. 47-10735). These electrophotographic organic photoconductors are improved with respect to mechanical characteristics and working properties to some extent in comparison with those of the inorganic photoconductors. However, generally the organic photoconductors are low in photosensitivity and accordingly do not satisfy sufficiently the requirements for electrophotographic photoconductors. Furthermore, the characteristics of electrophotographic photoconductors significantly depend upon materials used and preparation methods, in particular, upon photoconductive materials, and, therefore, photoconductive materials have been studied actively. In addition to the previously mentioned inorganic and organic photoconductors, photoconductive materials having high photosensitivities have been studied and developed, in which a material which generates charge carriers readily (hereinafter referred to as charge generation material) upon absorption of light is used in combination with a material which receives the generated charge carriers and transport the same (hereinafter referred to as charge transport material). However, satisfactory photoconductive materials have not yet been obtained.

The inventors of the present invention have discovered that the hydrazone compounds according to the present invention are particularly useful as the charge transfer materials.

Figure 2:
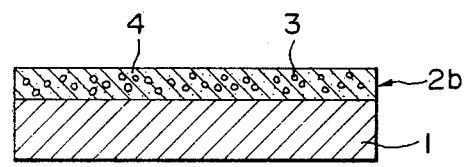
Figure 3:
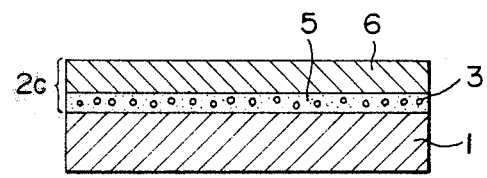
Figure 4:
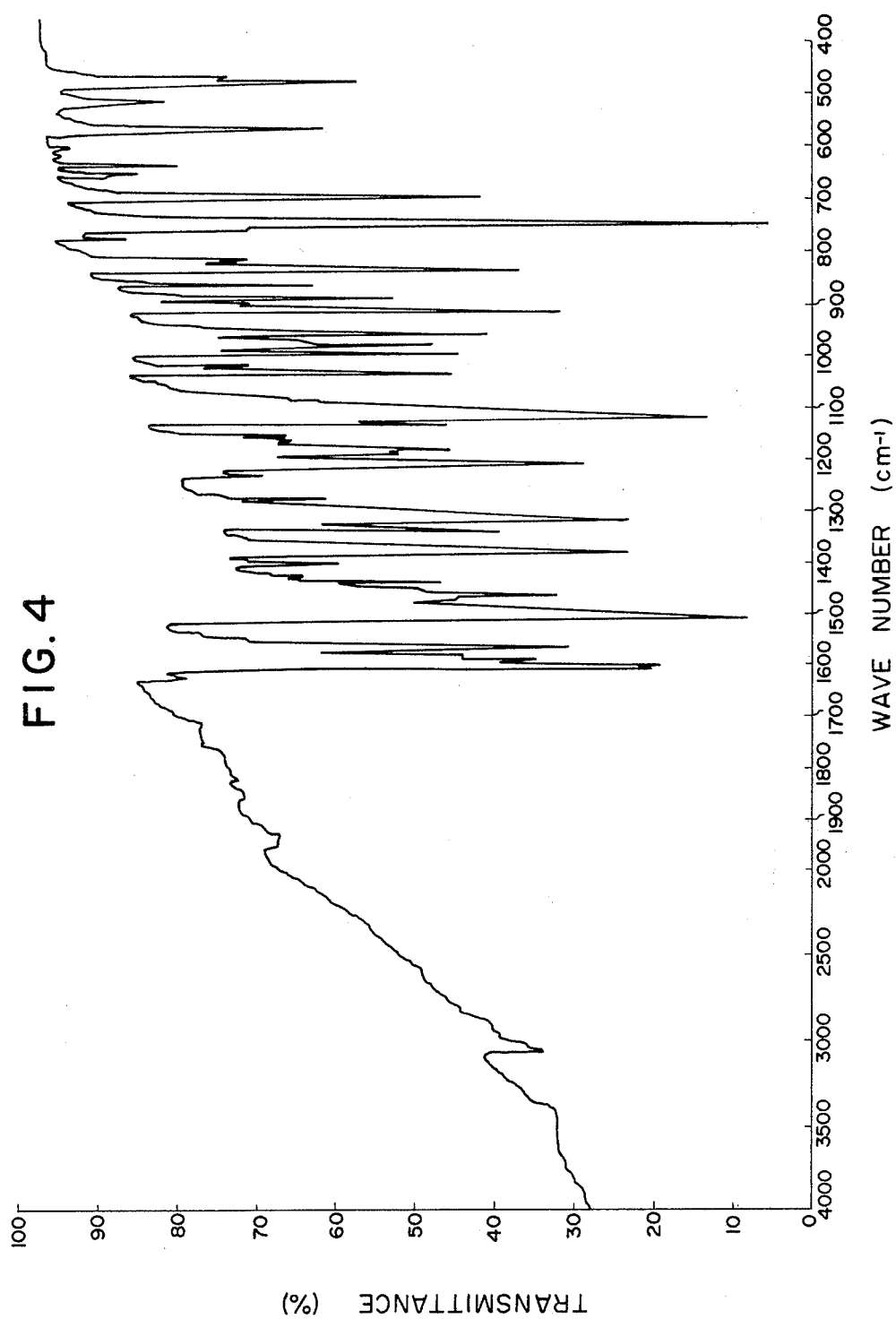
FIG. 4 through FIG. 9 are the infrared spectra of the novel hydrazone compounds according to the present invention.
Figure 5:
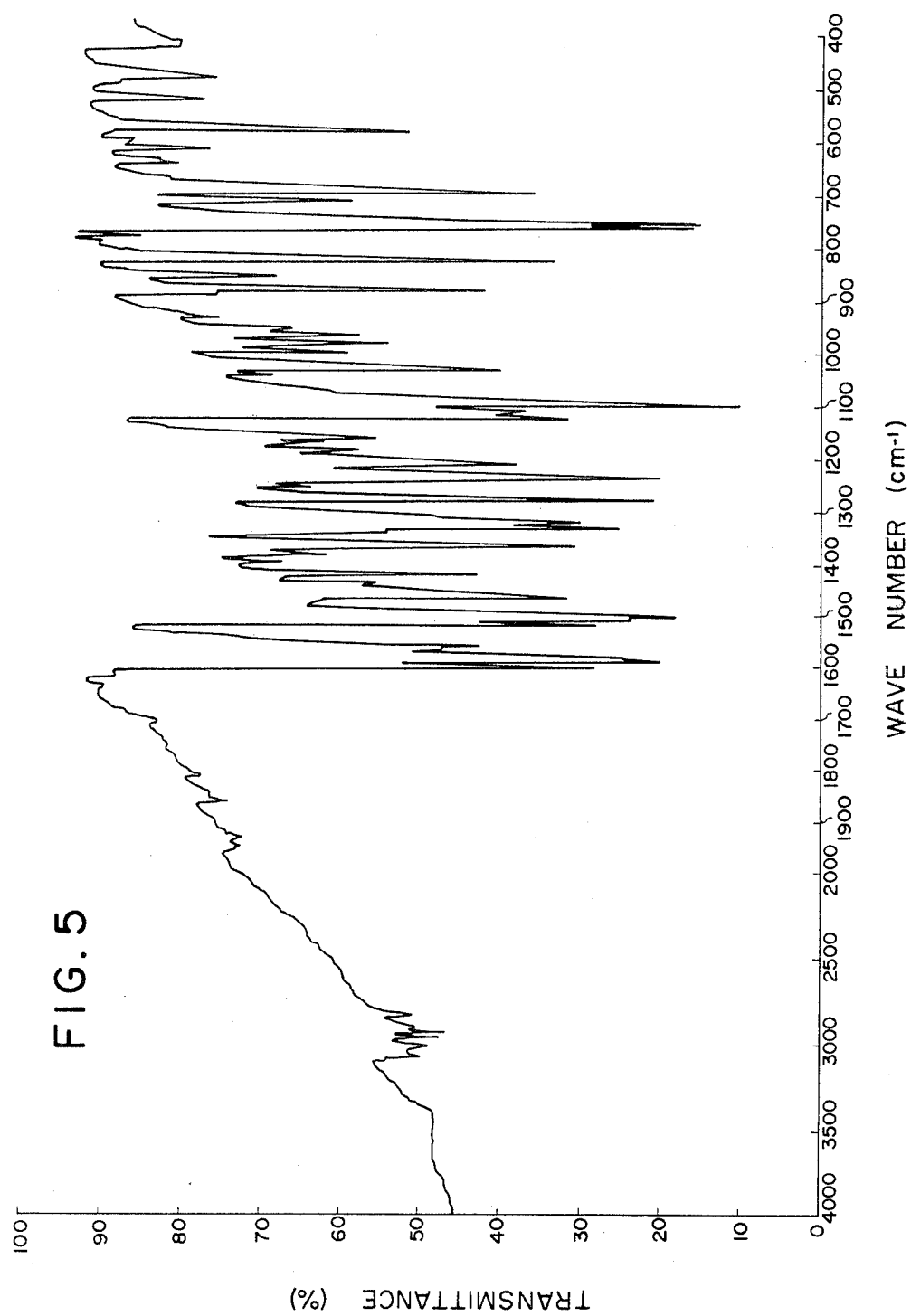
Figure 6:
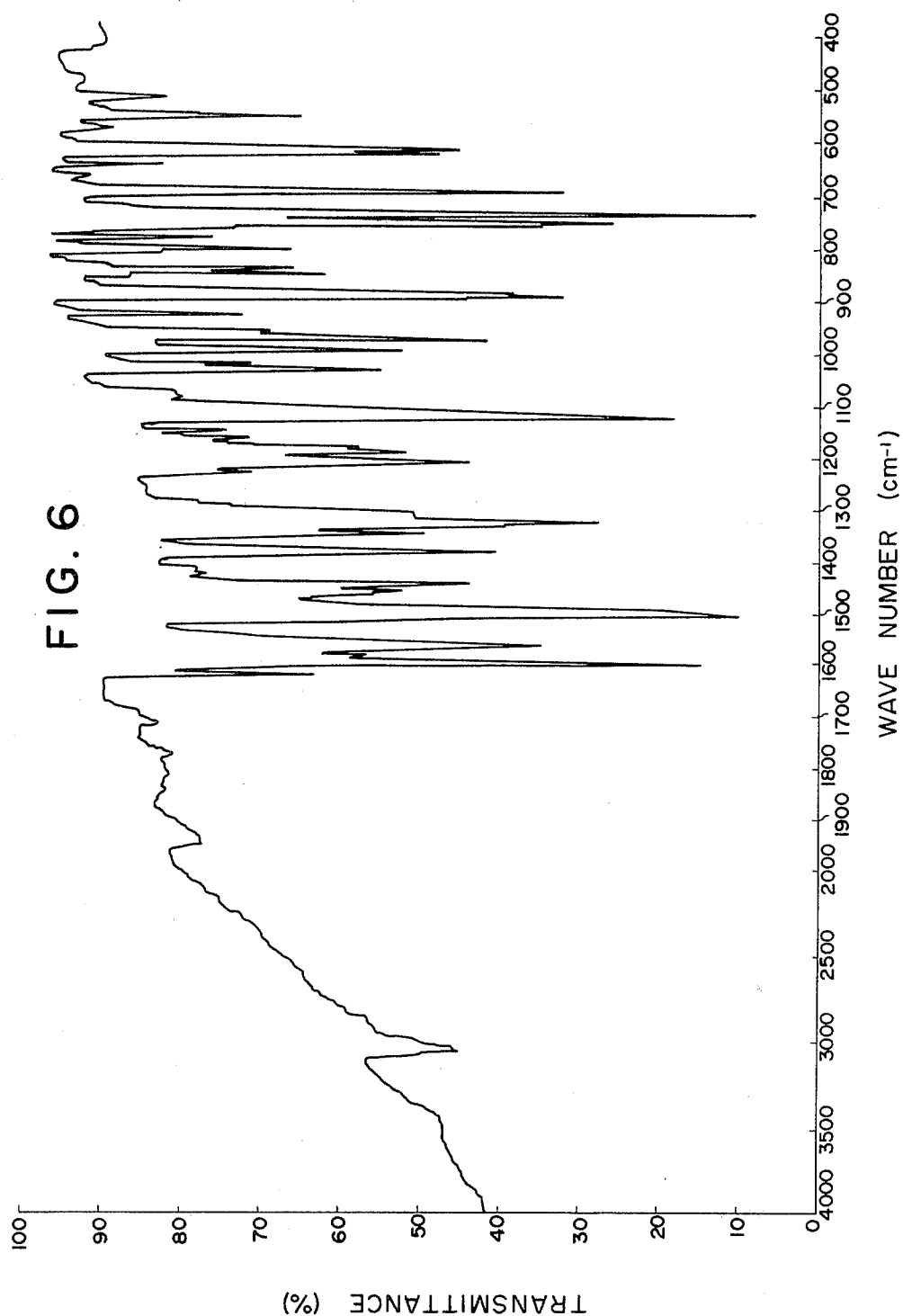
Figure 7:
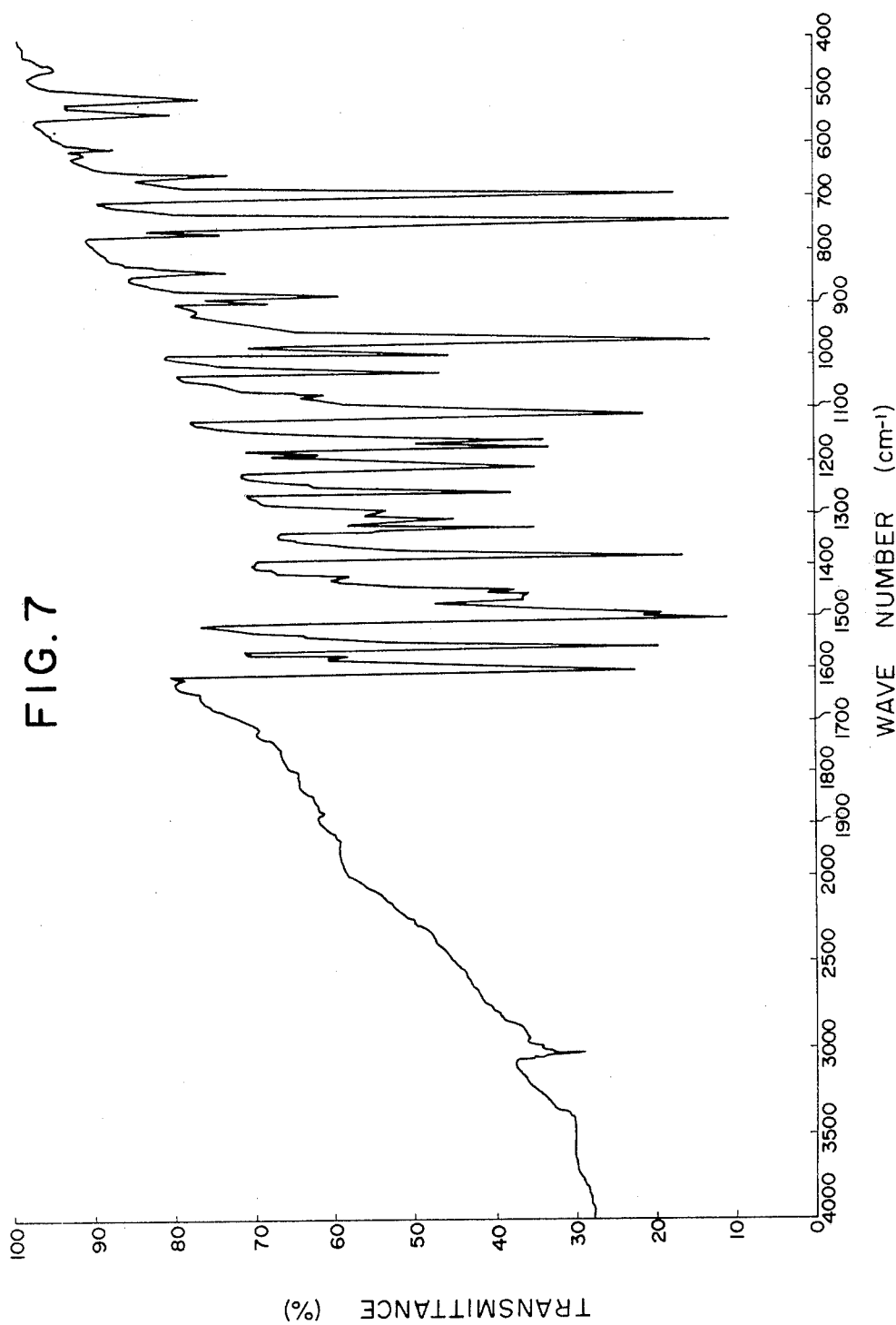
Figure 8:
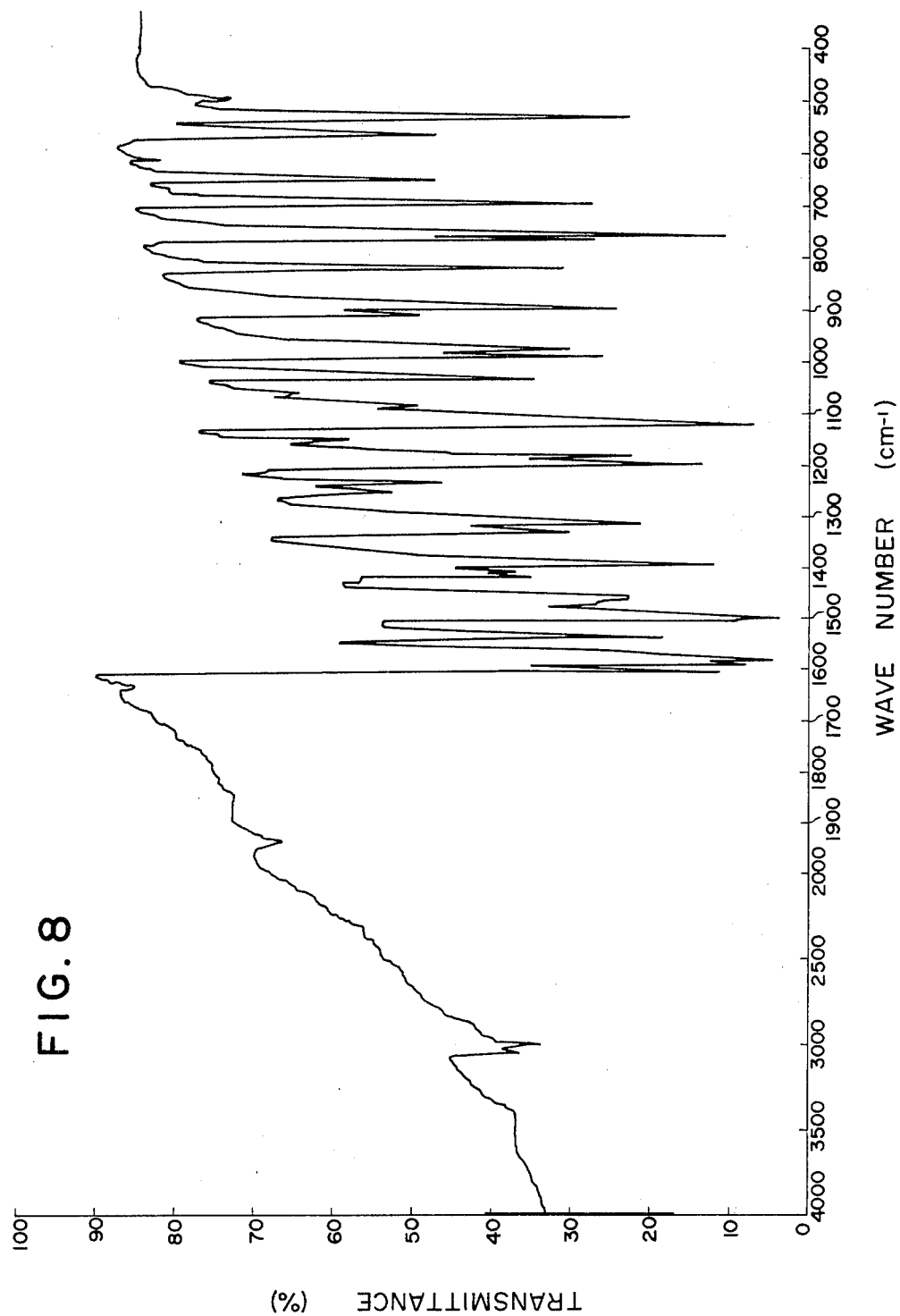
Figure 9:
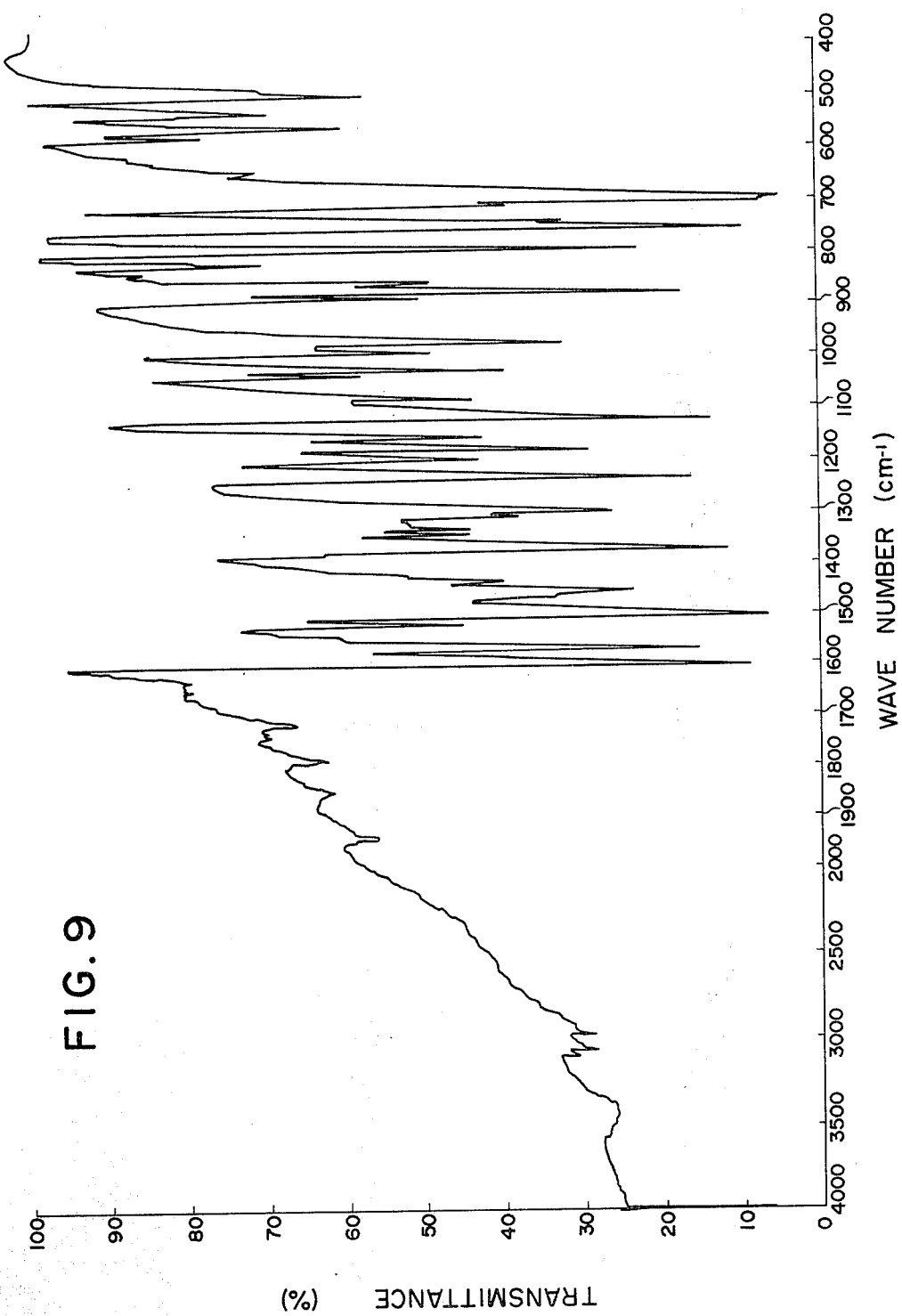

Referring to FIG. 1 through FIG. 3, there are shown specifically photoconductors in which the hydrazone compounds according to the present invention are employed.

The photoconductor shown in FIG. 1 comprises an electroconductive support material 1 and a photosensitive layer 2a comprising a hydrazone compound, a sensitizer dyestuff and a binder resin, the photosensitive layer 2a being formed on the electroconductive support material 1.

The photoconductor shown in FIG. 2 comprises an electroconductive support material 1 and a photosensitive layer 2b in which a charge generation material 3 is dispersed in a charge transport medium 4 consisting of a hydrazone compound and a binder material, the photosensitive layer 2b being formed on the electroconductive support material 1.

The photoconductor shown in FIG. 3 comprises an electroconductive support material 1 and a photosensitive layer 2c consisting of a charge generation layer 5 consisting essentially of the charge generation material 3 and a charge transport layer 6 containing a hydrazone compound.

EXAMPLE 15

This is an example of an electrophotographic photoconductor in which the hydrazone compound, 1-naphthaldehyde 1-methyl-1-phenylhydrazone, prepared in Example 1 is employed.

A mixture of 3 parts by weight of 4',4''-bis (2-hydroxy-3-phenylcarbomoyl-1-naphthylazo)-1,4-distyrylbenzene, 1 part by weight of a polyester resin (Trade name: polyester adhesive 4900 made by Du Pont) and 96 parts by weight of tetrahydrofuran was ground in a ball mill. This dispersion was coated on an aluminum evaporated polyester film by a doctor blade and was then dried at 80° C. for 5 minutes in a drying apparatus, so that a charge generation layer about 1μ thick was formed on the aluminium evaporated polyester film.

A solution consisting of 1 part by weight of 1-naphthaldehyde 1-methyl-1-phenylhydrazone prepared in Example 1, 1 part by weight of a polycarbonate resin and 8 parts by weight of tetrahydrofuran was coated on the charge generation layer by a doctor blade and was then dried at 100° C. for 10 minutes so that a charge transport layer about 10μ thick was formed on the charge generation layer.

The thus prepared electrophotographic photoconductor was charged negatively in the dark under application of −6 kV of corona charge for 20 seconds by a commercially available electrostatic copying sheet testing apparatus and was then allowed to stand in the dark for 20 seconds without applying any charge thereto, and the surface potential Vpo (V) of the photoconductor was measured. The photoconductor was then illuminated by a tungsten lamp in such a manner that the illuminance on the illuminated surface of the photoconductor was 20 lux, so that the exposure E½ (lux second) required to reduce the initial surface potential Vpo (V) to ½ the initial surface potential Vpo (V) was measured. the result showed that Vpo= −710 V and E½=2.8 lux. second.

The charge retention property in the dark and the photosensitivity of this photoconductor were excellent.

TABLE 1

| Example No. | Structural Formula | Melting Point | Element | Found | Calculated |
|---|---|---|---|---|---|
| 1 | Ph—N(CH₃)—N=CH—(naphthyl) | 92.5~94.5° C. | C (%)<br>H (%)<br>N (%) | 83.10<br>6.04<br>10.68 | 83.04<br>6.20<br>10.76 |
| 2 | Ph—N(CH₃)—N=CH—(naphthyl) | 172.5~174.5° C. | C (%)<br>H (%)<br>N (%) | 83.21<br>6.06<br>10.66 | 83.04<br>6.20<br>10.76 |
| 3 | Ph—N(CH₃)—N=CH—(naphthyl)—OCH₃ | 119.5~120.5° C. | C (%)<br>H (%)<br>N (%) | 78.89<br>6.12<br>9.52 | 78.59<br>6.25<br>9.65 |
| 4 | Ph—N(CH₃)—N=CH—(naphthyl with OCH₃) | 90.5~91.5° C. | C (%)<br>H (%)<br>N (%) | 78.97<br>6.18<br>9.59 | 78.59<br>6.25<br>9.65 |
| 5 | Ph—N(CH₃)—N=CH—(anthryl) | 162.0~162.5° C. | C (%)<br>H (%)<br>N (%) | 84.76<br>5.70<br>8.79 | 85.18<br>5.85<br>9.08 |
| 6 | Ph—N(CH₃)—N=CH—CH=CH—Ph | 113.5~114.5° C. | C (%)<br>H (%)<br>N (%) | 81.28<br>6.85<br>11.92 | 81.82<br>6.88<br>11.86 |

TABLE 1-continued

| Example No. | Structural Formula | Melting Point | Element Analysis | | |
|---|---|---|---|---|---|
| | | | Element | Found | Calculated |
| 7 | Ph-N(CH3)-N=CH-CH=CH-C6H4-N(CH3)2 | 174.0~177.0° C. | C (%)<br>H (%)<br>N (%) | 77.66<br>7.65<br>14.69 | 77.88<br>7.58<br>15.04 |
| 8 | Ph-N(CH3)-N=CH-CH=CH-C6H4(OCH3) | 100.5~101.5° C. | C (%)<br>H (%)<br>N (%) | 76.89<br>6.71<br>10.28 | 76.66<br>6.81<br>10.52 |
| 9 | Ph-N(CH3)-N=CH-C(CH3)=CH-Ph | 111.0~112.0° C. | C (%)<br>H (%)<br>N (%) | 81.88<br>7.27<br>10.98 | 81.56<br>7.25<br>11.19 |
| 10 | Ph-N(CH3)-N=CH-(pyridyl) | 53.0~55.0° C. | C (%)<br>H (%)<br>N (%) | 74.08<br>6.18<br>19.98 | 73.89<br>6.21<br>19.89 |
| 11 | Ph-N(CH3)-N=CH-(pyridyl) | 96.5~97.5° C. | C (%)<br>H (%)<br>N (%) | 74.24<br>6.11<br>20.05 | 73.89<br>6.21<br>19.89 |
| 12 | Ph-N(CH3)-N=CH-(pyridyl) | 81.5~82.0° C. | C (%)<br>H (%)<br>N (%) | 73.95<br>5.94<br>19.54 | 73.89<br>6.21<br>19.89 |
| 13 | Ph-N(CH3)-N=CH-(furyl) | 47.5~50.0° C. | C (%)<br>H (%)<br>N (%) | 71.71<br>5.91<br>13.78 | 71.97<br>6.05<br>14.00 |
| 14 | Ph-N(CH3)-N=CH-(thienyl) | 81.0~82.0° C. | C (%)<br>H (%)<br>N (%) | 66.91<br>5.57<br>12.89 | 66.62<br>5.60<br>12.95 |

What is claimed is:

1. A hydrazone compound having the formula

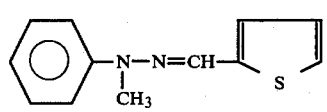

2. Hydrazone compounds having the general formula

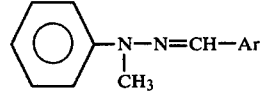

wherein Ar is a methoxy-substituted naphthalene ring radical.

3. A hydrazone compound having the formula

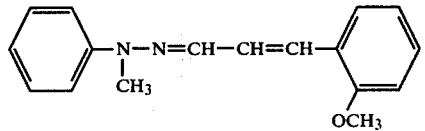

4. A hydrazone compound having the formula

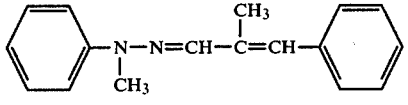

* * * * *

UNITED STATES PATENT AND TRADEMARK OFFICE
CERTIFICATE OF CORRECTION

PATENT NO. : 4,332,948            Page 1 of 2

DATED : June 1, 1982

INVENTOR(S) : KIYOSHI SAKAI ET AL

It is certified that error appears in the above—identified patent and that said Letters Patent is hereby corrected as shown below:

Column 2, line 8, delete "is" after "invention".

Column 2, line 26, change "AR" to --Ar--.

Column 3, line 21, delete "," after "When".

Column 3, line 34, change "an" to --a--.

Column 3, line 55, that portion of the formula reading "cH$_3$" should read --CH$_3$--.

Column 6, line 8, that portion of the formula reading "OHC.CH" should read --OHC-CH--.

Column 6, line 39, that portion of the formula reading "OHC.CH" should read --OHC-CH--.

Column 6, line 49, after "6.1" insert --g--.

Column 7, line 15, change "suctional" to --suction--.

Column 9, line 6, change "hield" to --yield--.

UNITED STATES PATENT AND TRADEMARK OFFICE
CERTIFICATE OF CORRECTION

PATENT NO. : 4,332,948
DATED : June 1, 1982
INVENTOR(S) : KIYOSHI SAKAI ET AL

It is certified that error appears in the above—identified patent and that said Letters Patent is hereby corrected as shown below:

Column 9, line 52, change "cadium" to --cadmium--.

Column 10, line 48, change "crystals" to --crystal--.

Column 11, line 2, change "transport" to --transports--.

Column 12, line 32, change "the" to --The--.

Signed and Sealed this

Fifth Day of October 1982

[SEAL]

Attest:

Attesting Officer

GERALD J. MOSSINGHOFF

Commissioner of Patents and Trademarks